United States Patent
Tajima et al.

(10) Patent No.: US 9,611,495 B2
(45) Date of Patent: Apr. 4, 2017

(54) BACTERIAL CELLULOSE AND BACTERIUM PRODUCING IT

(71) Applicants: Kenji Tajima, Sapporo-shi (JP); Ryota Kose, Fuchu-shi (JP)

(72) Inventors: Kenji Tajima, Sapporo (JP); Ryota Kose, Fuchu (JP); Hiroaki Sakurai, Obihiro (JP)

(73) Assignees: Kenji Tajima; Ryota Kose

( * ) Notice: Subject to any disclaimer, the term of this patent is extended or adjusted under 35 U.S.C. 154(b) by 0 days.

(21) Appl. No.: 14/655,862

(22) PCT Filed: Dec. 27, 2013

(86) PCT No.: PCT/JP2013/085163
§ 371 (c)(1),
(2) Date: Jun. 26, 2015

(87) PCT Pub. No.: WO2014/104318
PCT Pub. Date: Jul. 3, 2014

(65) Prior Publication Data
US 2015/0376666 A1    Dec. 31, 2015

(30) Foreign Application Priority Data
Dec. 28, 2012  (JP) .................................. 2012-289043

(51) Int. Cl.
C12P 19/04  (2006.01)
C08L 1/02   (2006.01)
C12R 1/01   (2006.01)

(52) U.S. Cl.
CPC .................. *C12P 19/04* (2013.01); *C08L 1/02* (2013.01); *C12R 1/01* (2013.01)

(58) Field of Classification Search
None
See application file for complete search history.

(56) References Cited

U.S. PATENT DOCUMENTS 5,962,277 A * 10/1999 Watanabe ............... C12P 19/04
                                                    435/101
2002/0040134 A1* 4/2002 Ishihara ................. B82Y 15/00
                                                    536/56

FOREIGN PATENT DOCUMENTS

CN    102168056 A    8/2011
JP    8-291201       11/1996
(Continued)

OTHER PUBLICATIONS

Japanese Office Action for Japanese Patent Application No. 2014-551859, mailed Dec. 17, 2014 (with English translation).
(Continued)

*Primary Examiner* — Robert Yamasaki
*Assistant Examiner* — Charles Zoltan Constantine
(74) *Attorney, Agent, or Firm* — RatnerPrestia

(57) ABSTRACT

[Problem]
To provide a bacterial cellulose which is highly dispersible in a liquid, shows excellent molding properties and high miscibility with other materials when applied to materials, and, therefore, has a high applicability as a practical material, and a bacterium which produces the bacterial cellulose.
[Solution]
A bacterial cellulose, water that contains said bacterial cellulose at a final concentration of 0.1±0.006 (w/w) showing a light transmittance at a wavelength of 500 nm of 35% or greater, and a bacterium producing the bacterial cellulose. According to the present invention, the bacterial cellulose that is uniformly dispersible in a liquid such as water can be obtained. The bacterial cellulose shows excellent molding properties and high miscibility with other materials and, therefore, can contribute to the improvement in the qualities of a final product or production efficiency thereof or to the reduction of production cost.

6 Claims, 12 Drawing Sheets

(56) References Cited

FOREIGN PATENT DOCUMENTS

| | | |
|---|---|---|
| JP | 2005-82704 | 3/2005 |
| JP | 2011-177172 | 9/2011 |
| WO | WO 2007/063854 A1 | 6/2007 |

OTHER PUBLICATIONS

Kose et al., Cellulose, 20:2971-79 (2013).
PCT/JP2013/085163 International Search Report issued by Japanese Patent Office Mar. 11, 2014.
Warashina et al., 2010 Cellulose R&D Abstracts at the 17th Annual Meeting of the Cellulose Society, p. 98, 2010 with English abstract.
Written Opinion of the International Search Report for PCT/JP2013/085163 dated Nov. 3, 2014.
Yoshinaga et al., Chemistry and Biology, 35(11):7-14 (1997) (with English translation).

\* cited by examiner

Figure 2-1

```
SIID9587       1:CATGCA-GTCGCACGAACCTTTCGGGGTTAGTGGCGGACGGGTGAGTAACCCGTAGGGAT 59
G. intermedius 1:CATGCAAGTCGCACGAACCTTTCGGGGTTAGTGGCGGACGGGTGAGTAACCCGTAGGGAT 60
                ******  ****************************************************

SIID9587       60:CTATCCACGGGTGGGGGATAACTTTGGGAAACTGAAGCTAATACCGCATGACACCTGAGG 119
G. intermedius 61:CTATCCACGGGTGGGGGATAACTTTGGGAAACTGAAGCTAATACCGCATGACACCTGAGG 120
                  ************************************************************

SIID9587       120:GTCAAAGGCGCAAGTCGCCTGTGGAGGAACCTGCGTTCGATTAGCTAGTTGGTGGGGTAA 179
G. intermedius 121:GTCAAAGGCGCAAGTCGCCTGTGGAGGAACCTGCGTTCGATTAGCTAGTTGGTGGGGTAA 180
                   ************************************************************

SIID9587       180:AGGCCTACCAAGGCGATGATCGATAGCTGGTCTGAGAGGATGATCAGCCACACTGGGACT 239
G. intermedius 181:AGGCCTACCAAGGCGATGATCGATAGCTGGTCTGAGAGGATGATCAGCCACACTGGGACT 240
                   ************************************************************

SIID9587       240:GAGACACGGCCCAGACTCCTACGGGAGGCAGCAGTGGGGAATATTGGACAATGGGCGCAA 299
G. intermedius 241:GAGACACGGCCCAGACTCCTACGGGAGGCAGCAGTGGGGAATATTGGACAATGGGCGCAA 300
                   ************************************************************

SIID9587       300:GCCTGATCCAGCAATGCCGCGTGTGTGAAGAAGGTTTTCGGATTGTAAAGCACTTTCAGC 359
G. intermedius 301:GCCTGATCCAGCAATGCCGCGTGTGTGAAGAAGGTTTTCGGATTGTAAAGCACTTTCAGC 360
                   ************************************************************

SIID9587       360:GGGGACGATGATCACGGTACCCGCAGAAGAAGCCCCGGCTAACTTCGTGCCAGCAGCCGC 419
G. intermedius 361:GGGGACGATGATCACGGTACCCGCAGAAGAAGCCCCGGCTAACTTCGTGCCAGCAGCCGC 420
                   ************************************************************

SIID9587       420:GGTAATACGAAGGGGGCAAGCGTTGCTCGGAATGACTGGGCGTAAAGGGCGCGTAGGCGG 479
G. intermedius 421:GGTAATACGAAGGGGGCAAGCGTTGCTCGGAATGACTGGGCGTAAAGGGCGCGTAGGCGG 480
                   ************************************************************

SIID9587       480:TTGACACAGTCAGATGTGAAATTCCCGGGCTTAACCTGGGGGCTGCATTTGATACGTGGC 539
G. intermedius 481:TTGACACAGTCAGATGTGAAATTCCCGGGCTTAACCTGGGGGCTGCATTTGATACGTGGC 540
                   ************************************************************

SIID9587       540:GACTAGAGTGTGAGAGAGGGTTGTGGAATTCCCAGTGTAGAGGTGAAATTCGTAGATATT 599
G. intermedius 541:GACTAGAGTGTGAGAGAGGGTTGTGGAATTCCCAGTGTAGAGGTGAAATTCGTAGATATT 600
                   ************************************************************

SIID9587       600:GGGAAGAACACCGGTGGCGAAGGCGGCAACCTGGCTCATAACTGACGCTGAGGCGCGAAA 659
G. intermedius 601:GGGAAGAACACCGGTGGCGAAGGCGGCAACCTGGCTCATGACTGACGCTGAGGCGCCGAAA 660
                   ************************************** *******************

SIID9587       660:GCGTGGGGAGCAAACAGGATTAGATACCCTGGTAGTCCACGCTGTAAACGATGTGTGCTG 719
G. intermedius 661:GCGTGGGGAGCAAACAGGATTAGATACCCTGGTAGTCCACGCTGTAAACGATGTGTGCTG 720
                   ************************************************************
```

Figure 2-2

```
SID9587         720:GATGTTGGGTGACTTTGTCATTCAGTGTCGTAGTTAACGCGATAAGCACACCGCCTGGGG 779
G. intermedius  721:GATGTTGGGTGACTTTGTCATTCAGTGTCGTAGTTAACGCGATAAGCACACCGCCTGGGG 780
                    ************************************************************

SID9587         780:AGTACGGCCGCAAGGTTGAAACTCAAAGGAATTGACGGGGGCCCGCACAAGCGGTGGAGC 839
G. intermedius  781:AGTACGGCCGCAAGGTTGAAACTCAAAGGAATTGACGGGGGCCCGCACAAGCGGTGGAGC 840
                    ************************************************************

SID9587         840:ATGTGGTTTAATTCGAAGCAACGCGCAGAACCTTACCAGGGCTTGACATGCGGAGGGTGT 899
G. intermedius  841:ATGTGGTTTAATTCGAAGCAACGCGCAGAACCTTACCAGGGCTTGACATGCGGAGGCCGT 900
                    ********************************************************  **

SID9587         900:GTCCAGAGATGGGCATTTCTCGCAAGAGACCTCCAGCACAGGTGCTGCATGGCTGTCGTC 959
G. intermedius  901:GTCCAGAGATGGGCATTTCTCGCAAGAGACCTCCAGCACAGGTGCTGCATGGCTGTCGTC 960
                    ************************************************************

SID9587         960:AGCTCGTGTCGTGAGATGTTGGGTTAAGTCCCGCAACGAGCGCAACCCTCGCCTTTAGTT 1019
G. intermedius  961:AGCTCGTGTCGTGAGATGTTGGGTTAAGTCCCGCAACGAGCGCAACCCTCGCCTTTAGTT 1020
                    ************************************************************

SID9587        1020:GCCATCACGTTTGGGTGGGCACTCTAAAGGAACTGCCGGTGACAAGCCGGAGGAAGGTGG 1079
G. intermedius 1021:GCCATCACGTTTGGGTGGGCACTCTAAAGGAACTGCCGGTGACAAGCCGGAGGAAGGTGG 1080
                    ************************************************************

SID9587        1080:GGATGACGTCAAGTCCTCATGGCCCTTATGTCCTGGGCTACACACGTGCTACAATGGCGG 1139
G. intermedius 1081:GGATGACGTCAAGTCCTCATGGCCCTTATGTCCTGGGCTACACACGTGCTACAATGGCGG 1140
                    ************************************************************

SID9587        1140:TGACAGTGGGAAGCCAGGTGGTGACACCGAGCCGATCTCAAAAAGCCGTCTCAGTTCGGA 1199
G. intermedius 1141:TGACAGTGGGAAGCCAGGTGGTGACACCGAGCCGATCTCAAAAAGCCGTCTCAGTTCGGA 1200
                    ************************************************************

SID9587        1200:TTGCACTCTGCAACTCGAGTGCATGAAGGTGGAATCGCTAGTAATCGCGGATCAGCATGC 1259
G. intermedius 1201:TTGCACTCTGCAACTCGAGTGCATGAAGGTGGAATCGCTAGTAATCGCGGATCAGCATGC 1260
                    ************************************************************

SID9587        1260:CGCGGTGAATACGTTCCCGGGCCTTGTACACACCGCCCGTCACACCATGGGAGTTGGTTT 1319
G. intermedius 1261:CGCGGTGAATACGTTCCCGGGCCTTGTACACACCGCCCGTCACACCATGGGAGTTGGTTT 1320
                    ************************************************************

SID9587        1320:GACCTTAAGCCGGTGAGCGAACCGCAAGGACGCAGCCGACCACC-TCG         1366
G. intermedius 1321:GACCTTAAGCCGGTGAGCGAACCGCAAGGACGCAGCCGACCACCGTCG         1368
                    ******************************************** ***
```

Figure 3

| TEST ITEM | SIID9587 |
|---|---|
| CULTURE TEMPERATURE (°C) | 30 |
| CELL MORPHOLOGY | BACILLUS (0.7-0.8 × 1.5-2.5 μm) |
| GRAM STAINABILITY | − |
| PRESENCE OR ABSENCE OF SPORE | − |
| MOBILITY | − |
| COLONY MORPHOLOGY | CULTURE MEDIUM : GYC AGAR<br>CULTURE TIME : 48 hr<br>DIAMETER : 1.0-2.0 mm<br>COLOR TONE : CREAM COLOR<br>SHAPE : CIRCULAR<br>RAISED STATE : HEMISPHERICAL<br>CIRCUMFERENCE : ENTIRE<br>SHAPE AND THE LIKE OF SURFACE : SMOOTH<br>DEGREE OF TRANSPARENCY : OPAQUE<br>VISCOSITY : BUTTER-LIKE |
| GROWTH TEMPERATURE TEST (°C) 37 | + |
| GROWTH TEMPERATURE TEST (°C) 45 | − |
| CATALASE REACTION | + |
| OXIDASE REACTION | − |
| ACID/GAS PRODUCTION FROM GLUCOSE (ACID PRODUCTION/GAS PRODUCTION) | NT |
| O/F TEST (OXIDATION/FERMENTATION) | NT |

+: POSITIVE, −: NEGATIVE, NT: Not test

| TEST ITEM | |
|---|---|
| PRODUCTION OF DYE IN GYC CULTURE MEDIUM | − |
| GROWTH UNDER ANAEROBIC CONDITION | |
| DECOMPOSITION OF SODIUM ACETATE INTO $CO_2$ | + |
| OXIDATION | |
| n-PROPANOL | + |
| GLUCOSE | + |
| ETHANOL | + |
| ASSIMILATION | |
| ETHANOL | + |
| GLYCERIN | + |
| SODIUM LACTATE | + |
| SACCHAROSE | +w |
| GROWTH IN 3% ETHANOL | + |
| GROWTH IN 5% ACETIC ACID | − |
| GROWTH IN 30% GLUCOSE-CONTAINING MEDIUM | + |
| GROWTH IN MRS AGAR | + |

+: POSITIVE, −: NEGATIVE

SEQUENCE LISTING

```
<160> NUMBER OF SEQ ID NOS: 1

<210> SEQ ID NO 1
<211> LENGTH: 1367
<212> TYPE: DNA
<213> ORGANISM: Gluconobacter intermedius SIID9587

<400> SEQUENCE: 1
catgcagtcg cacgaacctt tcggggttag tggcggacgg gtgagtaacg cgtagggatc      60
tatccacggg tggggataa ctttgggaaa ctgaagctaa taccgcatga cacctgaggg     120
tcaaaggcgc aagtcgcctg tggaggaacc tgcgttcgat tagctagttg gtggggtaaa    180
ggcctaccaa ggcgatgatc gatagctggt ctgagaggat gatcagccac actgggactg    240
agacacggcc cagactccta cgggaggcag cagtggggaa tattggacaa tgggcgcaag    300
cctgatccag caatgccgcg tgtgtgaaga aggttttcgg attgtaaagc actttcagcg    360
gggacgatga tgacggtacc cgcagaagaa gccccggcta acttcgtgcc agcagccgcg    420
gtaatacgaa gggggcaagc gttgctcgga atgactgggc gtaaagggcg cgtaggcggt    480
tgacacagtc agatgtgaaa ttcccgggct taacctgggg gctgcatttg atacgtggcg    540
actagagtgt gagagagggt tgtggaattc ccagtgtaga ggtgaaattc gtagatattg    600
ggaagaacac cggtggcgaa ggcggcaacc tggctcataa ctgacgctga ggcgcgaaag    660
cgtggggagc aaacaggatt agataccctg gtagtccacg ctgtaaacga tgtgtgctgg    720
atgttgggtg actttgtcat tcagtgtcgt agttaacgcg ataagcacac cgcctgggga    780
```

```
gtacggccgc aaggttgaaa ctcaaaggaa ttgacggggg cccgcacaag cggtggagca    840
tgtggtttaa ttcgaagcaa cgcgcagaac cttaccaggg cttgacatgc ggaggctgtg    900
tccagagatg ggcatttctc gcaagagacc tccagcacag gtgctgcatg gctgtcgtca    960
gctcgtgtcg tgagatgttg ggttaagtcc cgcaacgagc gcaaccctcg cctttagttg   1020
ccatcacgtt tgggtgggca ctctaaagga actgccggtg acaagccgga ggaaggtggg   1080
gatgacgtca agtcctcatg gcccttatgt cctgggctac acacgtgcta caatggcggt   1140
gacagtggga agccaggtgg tgacaccgag ccgatctcaa aaagccgtct cagttcggat   1200
tgcactctgc aactcgagtg catgaaggtg gaatcgctag taatcgcgga tcagcatgcc   1260
gcggtgaata cgttcccggg ccttgtacac accgcccgtc acaccatggg agttggtttg   1320
accttaagcc ggtgagcgaa ccgcaaggac gcagccgacc acgtcgt                 1367
```

BACTERIAL CELLULOSE AND BACTERIUM PRODUCING IT

CROSS-REFERENCE TO RELATED APPLICATIONS

This application is a U.S. National Phase Application of PCT International Application PCT/JP2013/085163, filed Dec. 27, 2013 which claims priority to Japanese Application No. 2012-289043, filed Dec. 28, 2012, the contents of which are incorporated herein by reference in their entireties for all purposes.

TECHNICAL FIELD

The present invention relates to a bacterial cellulose and a bacterium producing it, and particularly to a bacterial cellulose excellent in dispersibility in liquids and a bacterium producing it.

BACKGROUND OF THE INVENTION

A bacterial cellulose typically consists of a nanofiber having a width of about 50 nm, and has received attention as a material capable of being utilized in various industrial fields since it has characteristics, such as high mechanical strength and biocompatibility and biodegradability. The bacterial cellulose is typically obtained in the form of a film consisting of a gelled substance (hereinafter, referred to as "gelled film") on the culture medium surface by subjecting a bacterium, such as an acetic acid bacterium, to stationary culture; however, the gelled film has a problem, such as being poorly applicable as an actual material since it is poor in moldability and miscibility with other substances when applied to materials and high in cost because of being low in production efficiency.

To address such a problem, there is a need for a bacterial cellulose not in the form of a gelled film but dispersible in liquids and therefore excellent in applicability. For example, Non Patent Literature 1 discloses a bacterial cellulose obtained by subjecting *Acetobacter xylinum* subsp. *sucrofermentans* to aerated and agitated culture, and Non Patent Literature 2 also discloses a bacterial cellulose obtained by subjecting *Gluconacetobacter xylinum* strain JCM10150 to rotary shaking culture in a culture medium containing carboxymethyl cellulose (CMC).

CITATION LIST

Non Patent Literature

Non Patent Literature 1: Yoshinaga, et al., Kagaku To Seibutsu (Chemistry and Biology), vol. 35, no. 11, p. 7-14, 1997

Non Patent Literature 2: S. Warashina, et al., 2010 Cellulose R&D Abstracts at the 17th Annual Meeting of the Cellulose Society, p. 98, 2010

SUMMARY OF THE INVENTION

Technical Problem

However, the bacterial cellulose described in Non Patent Literature 1 is not high in dispersibility in water as is evident from the description that it is not one produced using a culture medium containing CMC having the effect of improving the dispersibility of a bacterial cellulose and that it is dispersed "in the form of tiny grains or fibers" in water (ibid; page 9, right column). Consequently, the bacterial cellulose is insufficient in terms of moldability and miscibility with other substances for practical use. The bacterial cellulose described in Non Patent Literature 2 is also not high in dispersibility in water since water containing the bacterial cellulose is higher in white turbidity at the bottom than at the top and has sedimentation observed and cellulose grains are visibly large (ibid; FIG. 1) in any of the cases where the amount of addition of CMC to the culture medium is 0.5%, 1%, and 2%. Consequently, this bacterial cellulose is insufficient in terms of moldability and miscibility with other substances, necessary for practical use.

Thus, the bacterial celluloses described in both of Non Patent Literatures 1 and 2 are insufficient in moldability as a material and miscibility with other substances, and also poor in practicability in terms of efficiency of material production.

The present invention has been made to solve such problems and an object thereof is to provide a bacterial cellulose high in dispersibility in liquids, favorable in moldability and miscibility with other materials in being put to practical use, and excellent in applicability as an actual material, and a bacterium producing the bacterial cellulose.

Solution to Problem

As a result of intensive studies, the present inventors have found that the bacterial cellulose is highly water-dispersible, which is obtained by subjecting the strain SIID9587 as a new strain of *Gluconacetobacter intermedius* (accession number NITE BP-01495) (hereinafter, sometimes referred to as "strain NEDO-01 (*G. intermedius* strain SIID9587)") to agitated culture in a CMC-containing culture medium using a glycerol-containing by-product generated in producing a biodiesel fuel from vegetable oil (Bio Diesel Fuel By-product; BDF-B, waste glycerin), reagent glycerol, or molasses as a carbon source, thereby accomplishing the following inventions.

(1) The bacterial cellulose according to the present invention has the physical characteristic of a transmittance of light at a wavelength of 500 nm of water containing the bacterial cellulose at a final concentration of $0.1 \pm 0.006\%$ (w/w) of 35% or more.

(2) The bacterial cellulose according to the present invention further has the physical characteristic of a retention volume of the peak top of the chromatogram in the gel permeation chromatography performed under the following conditions i) to vi) of from 2.5 mL inclusive to 3.0 mL exclusive:

i) column: a column 6.0 mm in inside diameter and 15 cm in length, packed with a methacrylate polymer having a particle diameter of 9 μm; ii) guard column: 4.6 mm in inside diameter and 3.5 cm in length; iii) column temperature: 35° C.; iv) feed flow rate: 0.07 mL/minute; v) eluent: a 40 to 42% (w/w) tetrabutylphosphonium hydroxide aqueous solution; and vi) final concentration of the bacterial cellulose in the eluent: 0.2% (w/w).

(3) The bacterial cellulose according to the present invention is preferably produced by the assimilation of BDF-B.

(4) The bacterial cellulose according to the present invention is preferably produced by the assimilation of 1 or 2 or more selected from the group consisting of sugar, a sucrose-containing by-product generated in producing sugar, and hydrolysates thereof, and isomerized sugar.

(5) The by-product is preferably molasses when the bacterial cellulose according to the present invention is produced by the assimilation of the sucrose-containing by-product generated in producing sugar.

(6) The bacterial cellulose according to the present invention may be one produced by *Gluconacetobacter intermedius*.

(7) The bacterial cellulose according to the present invention may be one produced by *Gluconacetobacter intermedius* strain SIID9587 (strain NEDO-01) (accession number NITE BP-01495).

(8) The bacterium according to the present invention is characterized by producing the bacterial cellulose according to any one of (1) to (5) above.

(9) The bacterium according to the present invention may be *Gluconacetobacter intermedius* strain SIID9587 (strain NEDO-01) (accession number NITE BP-01495) producing the bacterial cellulose according to any one of (1) to (5) above.

Advantageous Effects of Invention

The bacterial cellulose according to the present invention can provide a bacterial cellulose almost uniformly dispersible in liquids such as water, and can contribute to an improvement in the quality of the final product and production efficiency or a reduction in production cost since this bacterial cellulose is excellent in moldability and miscibility with other substances. The present invention can provide a bacterial cellulose almost uniformly dispersible in liquids by purification under mild conditions without requiring steps of refining with a mixer and the like, and can provide a bacterial cellulose having a relatively large average molecular weight. In addition, the present invention can contribute to effective resource utilization by using a sucrose-containing by-product generated in producing sugar, such as BDF-B or molasses, as a carbon source, and enables the achievement of the reduction of bacterial cellulose price. Further, the present invention can efficiently provide a large amount of a bacterial cellulose by production using *Gluconacetobacter intermedius* or *Gluconacetobacter intermedius* strain SIID9587 (strain NEDO-01).

BRIEF DESCRIPTION OF THE DRAWINGS

FIG. 2-1 is a diagram showing points of identity and difference between the 16S rDNA nucleotide sequences of the strain SIID9587 and *G. intermedius* strain TF2. In the figure, the points of identity in the nucleotide sequences are represented by *marks and the points of difference are represented by quadrangular boxes. In the figure, *G. intermedius* indicates *G. intermedius* strain TF2.

FIG. 2-2 is a diagram showing points of identity and difference between the 16S rDNA nucleotide sequences of the strain SIID9587 and *G. intermedius* strain TF2. In the figure, the points of identity in the nucleotide sequences are represented by *marks and the points of difference are represented by quadrangular boxes. In the figure, *G. intermedius* indicates *G. intermedius* strain TF2.

FIG. 3 is a pair of tables showing bacteriological properties of the strain SIID9587.

DETAILED DESCRIPTION OF THE INVENTION

Figure 1:
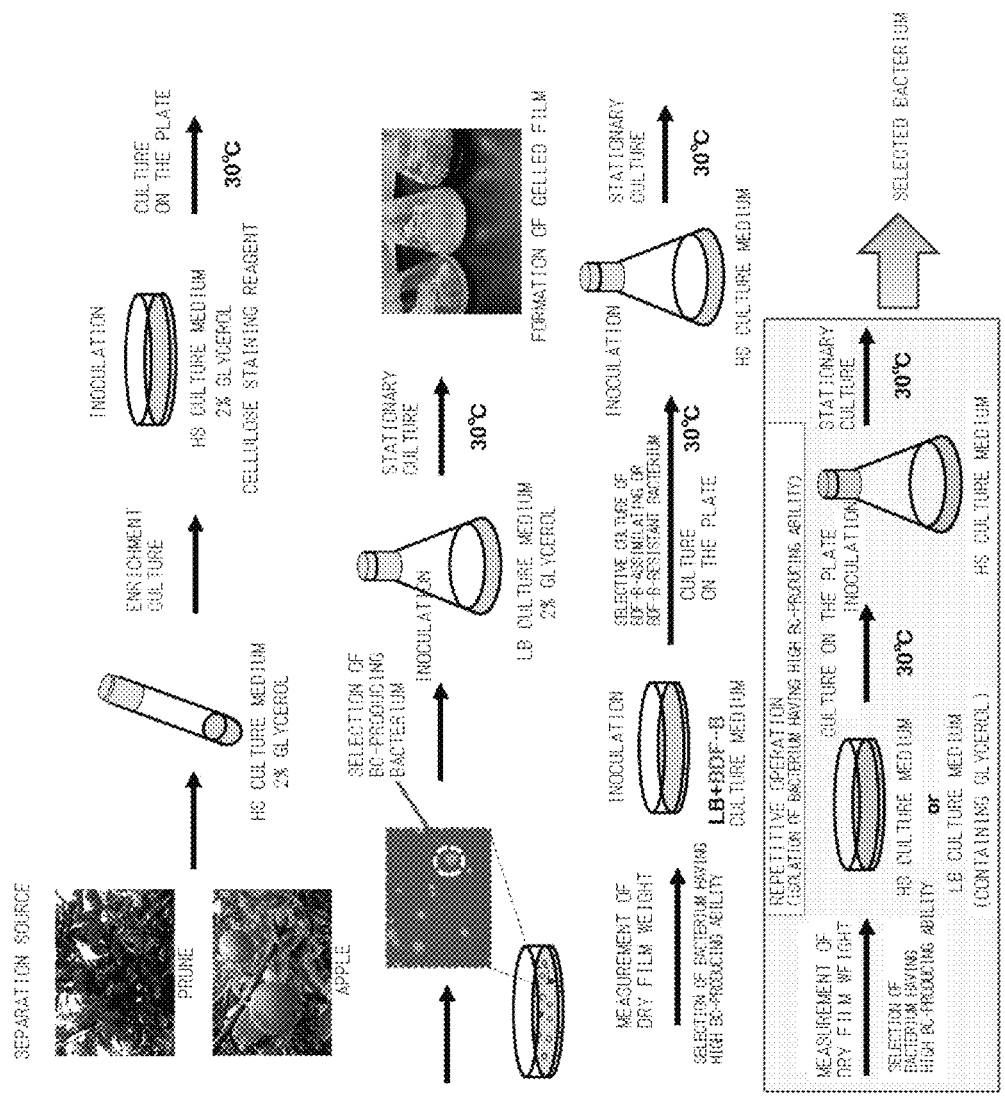
FIG. 1 is a flow diagram showing a protocol for isolating a bacterium producing a bacterial cellulose by assimilating BDF-B. In the figure, the bacterial cellulose is abbreviated as BC.

The bacterial cellulose according to the present invention and a bacterium producing it will be described below in detail. The bacterial cellulose according to the present invention refers to a cellulose produced by a bacterium.

For the purpose of the present invention, bacterial cellulose "being dispersed" in a liquid such as water refers to bacterial cellulose being floated or suspended in the liquid. The high dispersibility refers to, for example, the particle diameter or fiber width of a bacterial cellulose as a dispersoid being relatively small in a liquid, or the bacterial cellulose as a dispersoid being relatively uniformly floated or suspended in the liquid.

The bacterial cellulose according to the present invention has a high dispersibility in such an extent that it is almost uniformly dispersed in a liquid. Here, the liquid in which the bacterial cellulose is dispersed may be any of an organic solvent and an aqueous solvent; however, an aqueous solvent is preferable.

How high or low the dispersibility of a bacterial cellulose is can be measured, for example, using the light transmittance as an index; the relationship holds true that higher dispersibility results in a larger light transmittance and lower dispersibility results in a smaller light transmittance. The light transmittance can be determined by providing water containing the bacterial cellulose at a predetermined concentration to a spectrophotometer, irradiating the water with light at a predetermined wavelength, and measuring the amount of the transmitted light.

The bacterial cellulose according to the present invention has the physical characteristic of a transmittance of light at a wavelength of 500 nm of water containing the bacterial cellulose at a final concentration of 0.1±0.006% (w/w) of 35% or more. Here, examples of the transmittance of light at a wavelength of 500 nm of water containing the bacterial cellulose at a final concentration of 0.1±0.006% (w/w) according to the present invention can include 35% or more as well as 36% or more, 37% or more, 38% or more, 39% or more, 40% or more, 35% to 99% (both inclusive), 36% to 99% (both inclusive), 37% to 99% (both inclusive), 38% to 99% (both inclusive), 40% to 99% (both inclusive), 35% to 95% (both inclusive), 36% to 95% (both inclusive), 37% to 95% (both inclusive), 38% to 95% (both inclusive), 40% to 95% (both inclusive), 35% to 90% (both inclusive), 36% to 90% (both inclusive), 37% to 90% (both inclusive), 38% to 90% (both inclusive), 40% to 90% (both inclusive), 35% to 85% (both inclusive), 36% to 85% (both inclusive), 37% to 85% (both inclusive), 38% to 85% (both inclusive), 40% to 85% (both inclusive), 35% to 80% (both inclusive), 36% to 80% (both inclusive), 37% to 80% (both inclusive), 38% to 80% (both inclusive), and 40% to 80% (both inclusive).

The bacterial cellulose according to the present invention may also have a large average molecular weight compared to that of a plant-derived cellulose, such as a pulp-derived cellulose nanofiber. The average molecular weight of a cellulose can be measured using, for example, a chromatogram in the gel permeation chromatography as an index; the relationship holds true that a smaller molecular weight results in a larger retention volume of the peak top of such a chromatogram and a larger molecular weight results in a smaller retention volume. Specifically, the bacterial cellulose according to the present invention may have the physical characteristic of a retention volume of the peak top of the chromatogram in the gel permeation chromatography performed under the following conditions i) to vi) of from 2.5 mL inclusive to 3.0 mL exclusive: i) the column is a column 6.0 mm in inside diameter and 15 cm in length, packed with a methacrylate polymer having a particle diameter of 9 μm; ii) the guard column is 4.6 mm in inside diameter and 3.5 cm in length; iii) the column temperature is 35° C.; iv) the feed flow rate is 0.07 mL/minute; v) the eluent is a 40 to 42% (w/w) tetrabutylphosphonium hydroxide aqueous solution; and vi) the final concentration of the bacterial cellulose in the eluent is 0.2% (w/w).

The bacterial cellulose according to the present invention can be produced, for example, by causing a bacterium to produce a bacterial cellulose by culture in a culture medium containing a suitable carbon source.

Here, examples of the carbon source can include monosaccharides, such as glucose and fructose; disaccharides, such as sucrose, maltose, and lactose; oligosaccharides; sugar; sucrose-containing by-products generated in producing sugar, hydrolysates thereof, and isomerized sugar; saccharides, such as starch hydrolysates; mannitol; ethanol; acetic acid; citric acid; glycerol; and BDF-B. The carbon source can be properly set depending on the type of a bacterium, the culture conditions, the cost of production, and the like. BDF-B consists of 41.5% of glycerol, 21.4% of fatty acid, 12.4% of methanol, 6.3% of ignition residue, and 18.4% of others (Japan Food Research Laboratories) as a typical composition, and is a composition containing a large amount of glycerol available as a carbon source for a bacterium.

Here, sugar refers to a sweetener consisting essentially of sucrose (Kohjien, 6th Ed.), and, for the purpose of the present invention, may be a chemically synthesized one, or one produced using a natural product, such as sugar cane, sugar beet (white beet), sugar maple, gomuti (*Borassus flabellifer*), or sweet sorghum (*Sorghum bicolor dulciusculum*), as a raw material. Examples of the sugar according to the present invention can include non-centrifugal sugar, such as muscovado, shiroshita-to, casonade (brown sugar), wasanbon, or maple sugar, and centrifugal sugar, such as raw sugar or refined sugar. Examples of the refined sugar can include hard sugar, such as shirozara-to, coarse crystal medium soft sugar, or granulated sugar; soft sugar, such as white superior soft sugar or yellow soft sugar; processed sugar, such as cube sugar, crystal sugar, powdered sugar, or frost sugar; and liquid sugar.

The sucrose-containing by-product generated in producing sugar refers to one containing sucrose among by-products generated in a step of producing sugar, and specific examples thereof can include the pomace of natural raw materials, such as sugar cane and sugar beet as above described; molasses; and the residue generated in a purification step using filtration or ion-exchange resin.

The hydrolysate of a disaccharide, an oligosaccharide, sugar, or a sucrose-containing by-product generated in producing sugar refers to one obtained by subjecting the disaccharide, oligosaccharide, sugar, or sucrose-containing by-product generated in producing sugar to hydrolysis treatment, such as heating in an acidic solution.

The components in the culture medium other than the carbon source may be the same ones as those in well-known culture media used for the culture of bacteria, and preferably contain CMC. Specific examples of such a culture medium can include common nutrient culture media containing CMC, nitrogen sources, inorganic salts, and, as needed, organic trace nutrients, such as amino acids and vitamins. Examples of the nitrogen source can include organic or inorganic nitrogen sources, such as ammonium salts (e.g., ammonium sulfate, ammonium chloride, and ammonium phosphate), nitrates, urea, or peptone. Examples of the inorganic salt can also include phosphates, magnesium salts, calcium salts, iron salts, and manganese salts. Examples of the organic trace nutrient can include amino acids, vitamins, fatty acids, nucleic acids, and further peptone, casamino acids, yeast extracts, and soybean protein hydrolysates containing the nutrients. When an auxotrophic mutant requiring amino acids for growth is used, the required nutrients may further be supplemented.

The bacterium is not particularly limited provided that it can produce a bacterial cellulose; however, preferred is a bacterium capable of producing the bacterial cellulose under agitated culture or aerated culture, more preferably a bacterium assimilating BDF-B. Specific examples thereof can include bacteria of the genus *Acetobacter*, the genus *Gluconacetobacter*, the genus *Pseudomonas*, the genus *Agrobacterium*, the genus *Rhizobium*, and the genus *Enterobacter*. More specific examples thereof can include *Gluconacetobacter intermedius*, *Gluconacetobacter hansenii*, *Gluconacetobacter swingsii*, *Acetobacter pasteurianus*, *Acetobacter aceti*, *Acetobacter xylinum*, *Acetobacter xylinum* subsp. *sucrofermentans*, *Acetobacter xylinum* subsp. *nonacetoxidans*, *Acetobacter ransens*, *Sarcina ventriculi*, *Bacterium xyloides*, and *Enterobacter* sp.; however, among these, *Gluconacetobacter intermedius* is preferable. Still more specific examples thereof can include *Gluconacetobacter intermedius* strain SIID9587 (strain NEDO-01) (accession number NITE BP-01495), *Gluconacetobacter xylinus* strain ATCC53582, *Gluconacetobacter hansenii* strain ATCC23769, *Gluconacetobacter xylinus* strain ATCC700178 (BPR2001), *Gluconacetobacter swingsii* strain BPR3001E, *Acetobacter xylinum* strain JCM10150, and *Enterobacter* sp. strain CJF-002; among these, *Gluconacetobacter intermedius* strain SIID9587 (strain NEDO-01) (accession number NITE BP-01495) is preferable.

Culture methods can include, for example, agitated culture and aerated culture. Specific examples of the agitated culture can include culture using a fermenter, not involving aeration (non-aerated and agitated culture), culture using a fermenter, involving aeration (aerated and agitated culture), culture under swaying from side to side using a baffled flask (shake culture), and rotary culture using a baffled flask (rotation culture). The culture conditions may be well-known culture conditions used for the culture of the above bacteria; examples thereof can include culture conditions of an aeration volume of 1 to 10 L/minute, a rotation number of 100 to 800 rpm, a temperature of 20 to 40° C., and a culture period of 1 day to 7 days.

In the production of the bacterial cellulose according to the present invention, a step of pretreating a carbon source, a pre-preculture step, a preculture step, a step of purifying, drying, and suspending the bacterial cellulose, and the like may be carried out, as needed.

The bacterial cellulose according to the present invention can be used, for example, as an additive for paper strong agents, thickeners for food products, suspension stabilizers, and the like.

Then, the bacterium according to the present invention produces the above-described bacterial cellulose. For bacteria producing the bacterial cellulose according to the present invention, the same or equivalent components to those of the bacterial cellulose according to the present invention will not be described again.

The bacterial cellulose according to the present invention and a bacterium producing it will be described below based on Examples. However, the technical scope of the present invention is not intended to be limited to the features exhibited by these Examples.

EXAMPLES

Example 1

Isolation and Identification of Bacteria (1) Isolation of Bacteria

Bacteria producing a bacterial cellulose by assimilating BDF-B were isolated. Specifically, using the protocol shown in FIG. 1, enrichment culture was first carried out employing a culture medium containing 2% (w/v) of reagent glycerol (a guaranteed reagent from Wako Pure Chemical Industries Ltd.) in place of glucose in Hestrin-Schramm standard culture medium (composition; bacto pepton 0.5% (w/v), yeast extract 0.5% (w/v), $Na_2HPO_4$ 0.27% (w/v), citric acid 0.115% (w/v), glucose 2% (w/v); HS culture medium) (HS/glycerol culture medium) using apple and prune as separation sources. The resultant bacteria were inoculated on an HS/glycerol culture medium containing a cellulose staining reagent and cultured on plates at 30° C., and 15 bacterial strains producing bacterial celluloses were selected. Subsequently, these strains were inoculated on an LB culture medium (composition; trypsin 1% (w/v), yeast extract 0.5% (w/v), and sodium chloride 0.5% (w/v)) containing 2% (w/v) of reagent glycerol (a guaranteed reagent from Wako Pure Chemical Industries Ltd.) and subjected to stationary culture at 30° C. to form gelled films. The dry weight of the gelled films (hereinafter, referred to as "dry film weight") was measured, and 8 strains for which the dry film weight was large were selected as bacteria assimilating glycerol and having a high bacterial cellulose-producing ability. Then, these strains were inoculated on an LB culture medium containing BDF-B and cultured on plates at 30° C., and further inoculated on the HS culture medium and subjected to stationary culture at 30° C. to form gelled films. The operation of selecting a bacterial strain for which the dry film weight was large among these bacteria, culturing on plates with the glycerol-containing LB culture medium or the HS/glycerol culture medium, and then subjecting the resultant to stationary culture on the HS culture medium was repeated to select one bacterial strain having a BDF-B-assimilating property and having a high bacterial cellulose-producing ability, which was called strain SIID9587.

(2) Identification of Bacteria

Sequencing was carried out according to an ordinary method for the strain SIID9587 of 1 (1) of this Example to determine the nucleotide sequence of the full-length 16S rDNA (1367 bp; SEQ ID NO: 1). Subsequently, 16S rDNA nucleotide sequence analysis and bacteriological property test were performed in TechnoSuruga Laboratory Co., Ltd.

[2-1] 16S rDNA Nucleotide Sequence Analysis

The 16S rDNA nucleotide sequence analysis was carried out using Aporon 2.0 (TechnoSuruga Laboratory Co., Ltd.) as software and Aporon DB-BA 6.0 (TechnoSuruga Laboratory Co., Ltd.) and the International Nucleotide Sequence Databases (GenBank/DDBJ/EMBL) as databases. As a result of homology search with Aporon DB-BA 6.0, the 16S rDNA nucleotide sequence for the strain SIID9587 (SEQ ID NO: 1) was found to have high homology to the 16S rDNA nucleotide sequence for the genus *Gluconacetobacter* and have the highest homology to the 16S rDNA nucleotide sequence for *G. intermedius* strain TF2 (accession number Y14694) (homology rate: 99.8%). As a result of homology search with GenBank/DDBJ/EMBL, the 16S rDNA nucleotide sequence for the strain SIID9587 (SEQ ID NO: 1) was also found to have high homology to the 16S rDNA nucleotide sequence for the genus *Gluconacetobacter*, and that for the type strain was found to have high homology to the 16S rDNA nucleotide sequence for *G. intermedius* strain TF2 (accession number NR_026435) (homology rate: 99.8%).

Figure 4:
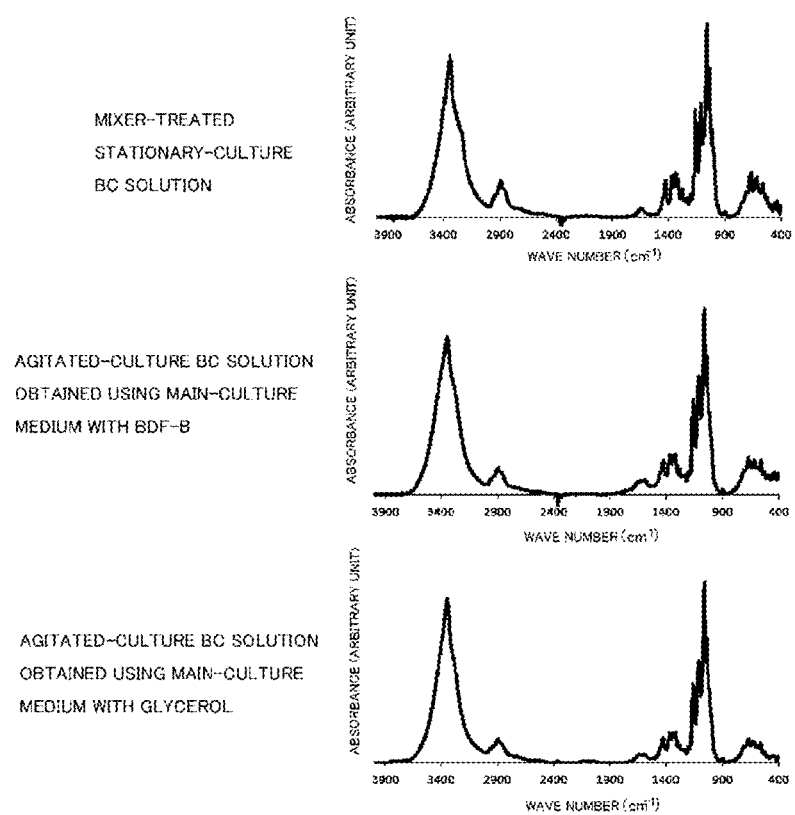
FIG. 4 is a series of charts showing IR spectra of a bacterial cellulose obtained by subjecting the strain NEDO-01 (*G. intermedius* strain SIID9587) to stationary culture (top chart) and products obtained by aerated and agitated culture using BDF-B and reagent glycerol as carbon sources (middle and bottom charts).

The sequence of the accession number Y14694 is identical to the sequence of the accession number NR_026435. The results of the comparison between the 16S rDNA nucleotide sequences for the strain SIID9587 and *G. intermedius* strain TF2 (accession number Y14694 or NR_026435) are shown in FIGS. 2-1 and 2-2. As shown in FIGS. 2-1 and 2-2, 4 nucleotides were different between both sequences. In homology search with Aporon DB-BA 6.0, as a result of simplified molecular phylogenetic analysis based on the 16S rDNA nucleotide sequences for the top 15 strains having high homology, the strain SIID9587 was found to be included in the cluster formed by the species of the genus *Gluconacetobacter*.

[2-2] Bacteriological Property Test

The results of bacteriological property test are shown in FIG. 3. As shown in FIG. 3, the strain SIID9587 was different in property in terms of not growing on a 5% acetic acid-containing culture medium from known *G. intermedius* and not different in other properties therefrom (BRENNER et al., Bergey's manual of Systematic Bacteriology. Vol. 2. The Proteobacteria, Part C The Alpha-, Beta-, Delta-, and Epsilonproteobacteria. 2005. Springer. p72-77).

The above results of (2) [2-1] and [2-2] of this Example 1 showed that the strain SIID9587 belonged to *Gluconacetobacter intermedius*. On the other hand, it was shown that the strain SIID9587 was a new strain of *G. intermedius* since differences exist in the 16S rDNA nucleotide sequence and the bacteriological property between the strain SIID9587 and *Gluconacetobacter intermedius* strain TF2 as the type strain for *G. intermedius* as described above. Accordingly, this bacterial strain was deposited in the National Institute of Technology and Evaluation, Patent Microorganisms Depositary (NITE-IPOD; #122, 2-5-8 Kazusakamatari, Kisarazu-shi, Chiba 292-0818, Japan) under the accession number NITE BP-01495, Dec. 21, 2012. Hereinafter, the *Gluconacetobacter intermedius* strain SIID9587 (accession number NITE BP-01495) is called strain NEDO-01 (*G. intermedius* strain SIID9587).

(3) Determination of Product

The strain NEDO-01 (*G. intermedius* strain SIID9587) was precultured to proliferate bacterial cells. Subsequently, the culture solution obtained by the preculture (preculture solution) was added to the HS culture medium (carbon source; glucose), which was then subjected to stationary culture at 30° C. for about 8 days to perform the main culture to form a gelled film on the culture medium surface. The infrared spectroscopy (IR) spectrum and x-ray diffraction profile of the gelled film were obtained and analyzed according to an ordinary method. As a result, the gelled film was shown to be a cellulose having a I-type crystal structure. As a result of obtaining and analyzing a scanning electron microscope image according to an ordinary method, cellulose fibers having a width of the nano order (cellulose nanofibers) were shown to form a network structure in the gelled film. From these results, the strain NEDO-01 (*G. intermedius* strain SIID9587) was determined to produce a cellulose.

Example 2

Evaluation of Product Obtained by Aerated and Agitated Culture (1) Preparation of Product by Aerated and Agitated Culture BDF-B was subjected to neutralization treatment and further subjected to autoclave treatment to provide pretreated BDF-B.

Culture media were prepared in which reagent glycerol (a guaranteed reagent from Wako Pure Chemical Industries Ltd.) was added in place of glucose as a carbon source in an HS culture medium containing 2% (w/v) CMC (chemical grade, from Wako Pure Chemical Industries Ltd.) and in which the pretreated BDF-B was added to a concentration of 2% (w/v) in place of glucose in the CMC-containing HS culture medium, and called a main-culture medium with glycerol and a main-culture medium with BDF-B, respectively. The strain NEDO-01 (*G. intermedius* strain SIID9587) was first precultured to proliferate bacterial cells. Then, the preculture solution was inoculated on 5 L each of the main-culture medium with glycerol and the main culture medium with BDF-B and using the fermenter, subjected to aerated and agitated culture for 4 days under conditions of an aeration volume of 7 to 10 L/minute, a rotation number of 200 to 800 rpm, and a temperature of 30° C. to perform main culture. A 1% (w/v) NaOH aqueous solution was added to the culture solution obtained by the main culture (main-culture solution), which was then shaken at 60° C. and 80 rpm for 4 to 5 hours to lyse bacterial cells. After subjecting the resultant to centrifugation, the supernatant was removed to recover the precipitate to remove water-soluble bacterial cell components. The operation of adding ultrapure water thereto, performing centrifugation, and then removing the supernatant was repeated until the pH of the precipitate in a wet state reaches 7 or less to purify the product, and the resultant was called an agitated-culture BC solution.

(2) Preparation of Bacterial Cellulose by Stationary Culture

A gelled film was obtained by the method described in (3) of Example 1 and cut to a size of about 1 cm×1 cm. Subsequently, a 1% (w/v) NaOH aqueous solution was added thereto, which was then shaken at 60° C. and 80 strokes/minute for 4 to 5 hours and then shaken overnight at 20° C. The liquid was removed by filtration using a metal gauze to recover a gelled film. The operation of adding ultrapure water thereto and shaking the resultant overnight at 20° C. was repeated until pH reaches 7 or less for purification, followed by suspension treatment using a mixer for several minutes, and the resultant was called a mixer-treated stationary-culture BC solution.

(3) Analysis

The agitated-culture BC solution of (1) of this Example 2 and the mixer-treated stationary-culture BC solution of (2) of this Example 2 were each added dropwise onto a silicon plate, dried, and then provided to an infrared spectrophotometer (FT/IR-4200; JASCO Corporation), and measured at a cumulative number of 32 and a resolution of 2 cm$^{-1}$ or 4 cm$^{-1}$ to provide an IR spectrum. The results are shown in FIG. 4. As shown in FIG. 4, the IR spectra of the agitated-culture BC solutions obtained using the main-culture medium with BDF-B and the main-culture medium with glycerol had similar shapes to the IR spectrum of the mixer-treated stationary-culture BC solution. From these results, the product obtained by subjecting the strain NEDO-01 (*G. intermedius* strain SIID9587) to agitated culture using BDF-B or reagent glycerol as a carbon source was determined to be a cellulose.

Example 3

Dispersibility of Bacterial Cellulose in Water (1) Appearance of Water Containing Bacterial Cellulose The agitated-culture BC solution using the main-culture solution with BDF-B of (1) of Example 2 and the mixer-treated stationary-culture BC solution of (2) of Example 2 were provided. Commercial pulp-derived cellulose nanofibers were added to water for dispersion, and the resultant was called a pulp-derived CNF solution. The agitated-culture BC solution, the mixer-treated stationary-culture BC solution, and the pulp-derived CNF solution were allowed to stand for 1 day, followed by observing their appearance. The results are shown in FIG. 5.

Figure 5:
FIG. 5 is a series of photographs showing the appearance of waters each containing bacterial celluloses obtained by subjecting the strain NEDO-01 (*G. intermedius* strain SIID9587) to aerated and agitated culture and stationary culture (left and middle) and a pulp-derived bacterial cellulose nanofiber (right).

As shown in FIG. 5, the cellulose precipitation was observed in the pulp-derived CNF solution. Massive bacterial cellulose was observed in the mixer-treated stationary-culture BC solution, showing that the dispersion state of the bacterial cellulose was non-uniform. In contrast, in the agitated-culture BC solution, no precipitation or massive bacterial cellulose was observed and the bacterial cellulose was observed to be in the state of being uniformly dispersed. These results showed that the bacterial cellulose obtained by subjecting the strain NEDO-01 (G. intermedius strain SIID9587) to agitated culture had high dispersibility and was uniformly dispersed in a liquid, such as water, compared to the bacterial cellulose obtained by subjecting the pulp-derived cellulose nanofibers or the strain NEDO-01 (G. intermedius strain SIID9587) to stationary culture.

(2) Light Transmittance of Water Containing Bacterial Cellulose

[2-1] Comparison Between Bacterial Cellulose Obtained by Stationary Culture and Pulp-Derived Cellulose In the method described in (1) of Example 2, rotation culture was performed under conditions of 150 rpm and a temperature of 30° C. for 3 days using a baffled flask in place of the fermenter as main culture to prepare agitated-culture BC solutions, which were called sample A (obtained using the main-culture medium with glycerol) and sample B (obtained using the main-culture medium with BDF-B). The agitated-culture BC solution obtained using the Main-culture medium with BDF-B of (1) of Example 2 was called sample C, and the agitated-culture BC solution obtained using the main-culture medium with glycerol was called sample D. The mixer-treated stationary-culture BC solution of (2) of Example 2 and the pulp-derived CNF solution of (1) of Example 3 were provided. These solutions were adjusted to a final cellulose concentration of 0.1±0.006% (w/w) and 1 mL each thereof were added to cells and subjected to a spectrophotometer (U-2001 double-beam spectrophotometer; Hitachi, Ltd.) to measure the transmittance of light at a wavelength of 500 nm. A polyethylene disposable cuvette (semi-micro, having a light path length of 10 mm and a light path width of 4 mm) was used as each cell, and ultrapure water was used as a reference. The results are shown in Table 1.

[2-2] Comparison Between Presence and Absence of CMC in Culture Medium

In the method described in (1) of Example 2, the HS culture medium containing 2% (w/v) CMC and the HS culture medium containing no CMC were each used to provide agitated-culture BC solutions. However, molasses was used in place of glucose as a carbon source. When molasses was used as a carbon source, the number of days in the main culture was set to 3 days in place of 4 days since the carbon source in the culture medium virtually disappeared at day 3 of the main culture. Subsequently, the light transmittance of bacterial cellulose-containing waters was measured by the method described in (2) [2-1] of Example 3. The results are shown in the following Table 2.

TABLE 2

| CMC in Culture Medium | Culture Method | Carbon Source | Transmittance (%) |
|---|---|---|---|
| Contain | Agitated culture | Molasses | 57 |
| Not Contain | Agitated culture | Molasses | 18 |

As shown in Table 2, the transmittance when the HS culture medium containing CMC was used was 57%, whereas the transmittance when the HS culture medium containing no CMC was used was 18%.

The above results of (2) [2-1] and [2-2] of this Example 3 showed that the water containing the bacterial cellulose obtained by subjecting the strain NEDO-01 (G. intermedius strain SIID9587) to agitated culture in the CMC-containing culture medium at a final concentration of 0.1±0.006% (w/w) had a transmittance of light at a wavelength of 500 nm of 40% to 80% (both inclusive). In other words, the agitated culture of the strain NEDO-01 (G. intermedius strain SIID9587) in the CMC-containing culture medium was shown to provide a bacterial cellulose having a prominently high dispersibility in a liquid and uniformly dispersible in the liquid.

Example 4

Comparison in Transmittance and Bacterial Cellulose Production Rate Between Different Carbon Sources Agitated-culture BC solutions were each obtained by the method described in (1) of Example 2. However, molasses

TABLE 1

| | Culture Method | Carbon Source | Final Concentration of Cellulose (% (w/w)) | Transmittance (%) |
|---|---|---|---|---|
| Sample A | Agitated culture (Baffled Flask) | Reagent Glycerol | 0.10505 | 74.75 |
| Sample B | Agitated culture (Baffled Flask) | BDF-B | 0.10309 | 70.53 |
| Sample C | Agitated culture (Fermenter) | BDF-B | 0.09570 | 63.82 |
| Sample D | Agitated culture (Fermenter) | Reagent Glycerol | 0.10375 | 49.66 |
| Mixer-Treated Stationary-culture BC Solution | Stationary culture | Glucose | 0.09964 | 19.19 |
| Pulp-Derived CNF Solution | | | 0.10514 | 12.72 |

As shown in Table 1, the transmittance of the samples A, B, C, and D was 74.75%, 70.53%, 63.82%, and 49.66%, respectively, prominently high compared to 19.19% for the mixer-treated stationary-culture BC solution and 12.72% for the pulp-derived CNF solution, and roughly in the range of from 40% to 80% (both inclusive).

and reagent glycerol were used as carbon sources in place of glucose. When molasses was used as a carbon source, the number of days in the main culture was set to 3 days in place of 4 days. Subsequently, the light transmittance of each bacterial cellulose-containing water was measured by the method described in (2) [2-1] of Example 3. The agitated-culture BC solution was dried to measure the absolute dry weight of the bacterial cellulose, and the concentration of the bacterial cellulose per 1 L of the culture medium was calculated based on the measurement results and defined as the amount of the bacterial cellulose produced (amount of BC produced; g/L). A value provided by dividing the amount of BC produced by the number of days in the main culture is calculated, and the value was defined as the bacterial cellulose production rate (BC production rate; g/L/day). The results are shown in FIG. 6.

Figure 6:
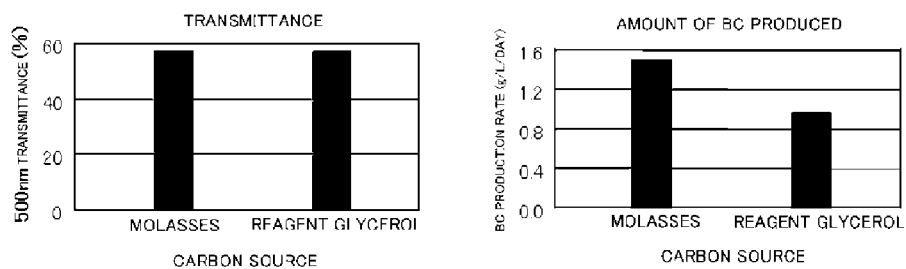
FIG. 6 is a series of drawings showing the light transmittance at a wavelength of 500 nm of waters containing bacterial celluloses obtained by subjecting strain NEDO-01 (*G. intermedius* strain SIID9587) to aerated and agitated culture using molasses and reagent glycerol as carbon sources, respectively, and the amount of the bacterial cellulose produced (amount of the BC produced) and the rate of production thereof (BC production rate).

As shown in the table and left bar graph of FIG. 6, the transmittance when molasses was used as a carbon source was 57% and was the same (57%) as that when reagent glycerol was used as a carbon source. These results showed that the culture of the strain NEDO-01 (*G. intermedius* strain SIID9587) using molasses as a carbon source provided a bacterial cellulose having a high light transmittance at a wavelength of 500 nm of water containing the bacterial cellulose at a final concentration of 0.1±0.006% (w/w) and was the same as when reagent glycerol was used as a carbon source. In other words, the culture of the strain NEDO-01 (*G. intermedius* strain SIID9587) using molasses as a carbon source was shown to provide a bacterial cellulose having high dispersibility and uniformly dispersible in a liquid.

As shown in the table and right bar graph of FIG. 6, the BC production rate when molasses was used as a carbon source was 1.48 g/L/day and was about 1.5 times higher than that (0.95 g/L/day) when reagent glycerol was used as a carbon source. These results showed that the culture of the strain NEDO-01 (*G. intermedius* strain SIID9587) using molasses as a carbon source provided a bacterial cellulose having high dispersibility in high amounts in a short period of time.

Example 5

Comparison in Transmittance and Bacterial Cellulose Production Rate Between Different Bacteria An agitated-culture BC solution was obtained by the method described in (1) of Example 2. However, molasses was used as a carbon source in place of glucose. The strain NEDO-01 (*G. intermedius* strain SIID9587) and *Gluconacetobacter hansenii* strain ATCC23769, *Gluconacetobacter xylinus* strain ATCC53582, *Gluconacetobacter xylinus* strain ATCC700178 (BPR2001), *Gluconacetobacter xylinus* strain JCM10150, *Gluconacetobacter intermedius* strain DSM11804, and *Gluconacetobacter xylinus* strain KCCM40274 as known bacterial cellulose-producing bacteria were used as bacteria, respectively. When the strain NEDO-01 (*G. intermedius* strain SIID9587) was used, the number of days in the main culture was set to 3 days in place of 4 days since the carbon source in the culture medium virtually disappeared at day 3 of the main culture. On the other hand, when the strain DSM11804 was used, the number of days in the main culture was set to 5 days in place of 4 days since the decrease in the carbon source in the culture medium was small in magnitude even at day 4 of the main culture. Subsequently, the light transmittance of each bacterial cellulose-containing water was measured by the method described in (2) [2-1] of Example 3. The amount of BC produced (g/L) and the BC production rate (g/L/day) were calculated by the method described in Example 4, and the transmittance and the BC production rate were quantified in bar graphs. The results are shown in FIG. 7.

Figure 7:
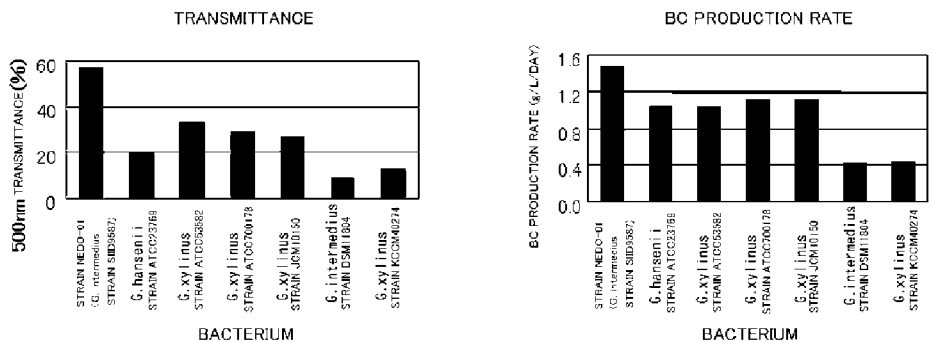
FIG. 7 is a series of drawings showing the light transmittance at a wavelength of 500 nm of waters containing bacterial celluloses obtained by subjecting strain NEDO-01 (*G. intermedius* strain SIID9587) and the known bacterial cellulose-producing bacteria *G. hansenii* strain ATCC23769, *G. xylinus* strain ATCC53582, *G. xylinus* strain ATCC700178 (BPR2001), *G. xylinus* strain JCM10150, *G. intermedius* strain DSM11804, and *G. xylinus* strain KCCM40274 to aerated and agitated culture, and the amount of the BC produced, the BC production rate, and the BC production rate ratio.

As shown in the table and left bar graph of FIG. 7, the transmittance when the strain NEDO-01 (*G. intermedius* strain SIID9587) was used was 57%, whereas the transmittance when *G. hansenii* strain ATCC23769, *G. xylinus* strain ATCC53582, *G. xylinus* strain ATCC700178 (BPR2001), *G. xylinus* strain JCM10150, *G. intermedius* strain DSM11804, and *G. xylinus* strain KCCM40274 were used was 20%, 33%, 29%, 27%, 9%, and 13%, respectively. These results showed that the transmittance of light at a wavelength of 500 nm of the water containing the bacterial cellulose obtained by culturing the strain NEDO-01 (*G. intermedius* strain SIID9587) at a final concentration of 0.1±0.006% (w/w) was prominently high (35% or more) compared to the light transmittance of the water containing the bacterial cellulose obtained by culturing each of the strains other than NEDO-01 (*G. intermedius* strain SIID9587). In other words, the culture of the strain NEDO-01 (*G. intermedius* strain SIID9587) was shown to be capable of providing a bacterial cellulose having high dispersibility and uniformly dispersible in a liquid.

As shown in the table and right bar graph of FIG. 6, the BC production rate when the strain NEDO-01 (*G. intermedius* strain SIID9587) was used was 1.48 g/L/day, whereas the BC production rate when *G. hansenii* strain ATCC23769, *G. xylinus* strain ATCC53582, *G. xylinus* strain ATCC700178 (BPR2001), *G. xylinus* strain JCM10150, *G. intermedius* strain DSM11804, and *G. xylinus* strain KCCM40274 were used was 1.05 g/L/day, 1.03 g/L/day, 1.11 g/L/day, 1.10 g/L/day, 0.42 g/L/day, and 0.43 g/L/day, respectively. In other words, the BC production rate when the strain NEDO-01 (*G. intermedius* strain SIID9587) was used was prominently high compared to the BC production rate when the strains other than NEDO-01 (*G. intermedius* strain SIID9587) were used. These results showed that the culture of the strain NEDO-01 (*G. intermedius* strain SIID9587) could provide a bacterial cellulose having high dispersibility in high amounts in a short period of time.

Example 6

Molecular Weight of Bacterial Cellulose

Figure 8:
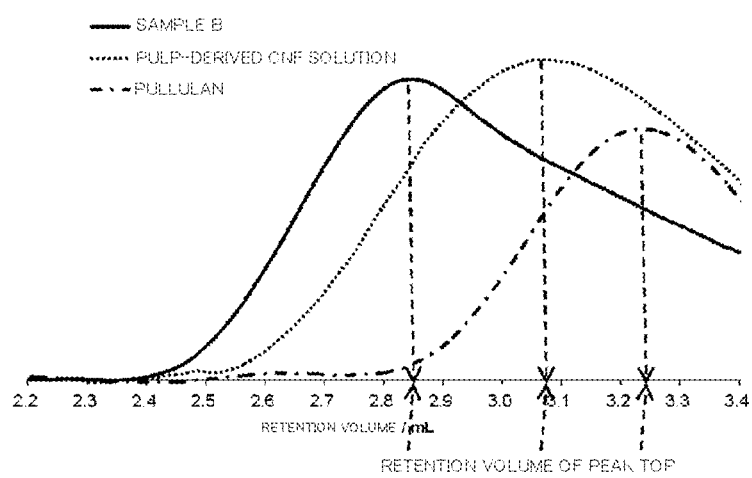
FIG. 8 is a chart showing chromatograms of the gel permeation chromatography of a bacterial cellulose obtained by subjecting strain NEDO-01 (*G. intermedius* strain SIID9587) to rotation culture using BDF-B as a carbon source (sample B), a pulp-derived cellulose nanofiber (pulp-derived CNF solution), and pullulan.

The samples A, B, C, and D and pulp-derived CNF solution of (2) of Example 3 were provided as samples. These samples were each freeze-dried, added to a 57 to 59% tetrabutylphosphonium hydroxide aqueous solution, and dissolved by standing at 35° C., followed by adding water to a tetrabutylphosphonium hydroxide concentration of 40 to 42% (w/w) and a sample concentration of 0.2% (w/w). Subsequently, centrifugation was carried out to precipitate impurities to recover the supernatant. The supernatant was subjected to the gel permeation chromatography under the following conditions to measure the retention volume of the peak top of the chromatogram. The supernatant was measured 3 times under the same conditions. The results are shown in Table 3, and a randomly selected chromatogram is shown in FIG. 8.

Condition for Gel Permeation Chromatography
  Instrument; high-performance liquid chromatograph (Shimadzu Corporation)
  Column; a column 6.0 mm in inside diameter and 15 cm in length, packed with a methacrylate polymer having a particle diameter of 9 μm (TSKgel super AWM-H; Tosoh Corporation) Guard column; 4.6 mm in inside diameter and 3.5 cm in length (TSK guardcolum super AW-H; Tosoh Corporation)
  Column temperature; 35° C.
  Feed flow rate; 0.07 mL/minute
  Sample injection volume; 10 μL Eluent; a 40 to 42% (w/w) tetrabutylphosphonium hydroxide aqueous solution Final concentration of bacterial cellulose in the eluent; 0.2% (w/w)

Control sample; pullulan having a molecular weight of $85.3 \times 10^4$ (Shodex standard P-82)

TABLE 3

|  | Retention Time/Minute | Retention Volume/mL | Average/ mL | Standard Deviation/ mL |
|---|---|---|---|---|
| Sample A (1st) | 40.4 | 2.828 | 2.79 | 0.05 |
| Sample A (2nd) | 39.1 | 2.737 | | |
| Sample A (3rd) | 40 | 2.8 | | |
| Sample B (1st) | 39.8 | 2.786 | 2.81 | 0.03 |
| Sample B (2nd) | 39.9 | 2.793 | | |
| sample B (3rd) | 40.7 | 2.849 | | |
| Sample C (1st) | 40.1 | 2.807 | 2.82 | 0.02 |
| Sample C (2nd) | 40.5 | 2.835 | | |
| Sample C (3rd) | 40.1 | 2.807 | | |
| Sample D (1st) | 39.2 | 2.744 | 2.76 | 0.02 |
| Sample D (2nd) | 39.4 | 2.758 | | |
| Sample D (3rd) | 39.8 | 2.786 | | |
| Pulp-derived CNF Solution (1st) | 42.9 | 3.003 | 3.04 | 0.04 |
| Pulp-derived CNF Solution (2nd) | 43.4 | 3.038 | | |
| Pulp-derived CNF Solution (3rd) | 43.9 | 3.073 | | |
| Pullulan (1st) | 45.7 | 3.199 | 3.24 | 0.04 |
| Pullulan (2nd) | 46.8 | 3.276 | | |
| Pullulan (3rd) | 46.4 | 3.248 | | |

As shown in Table 3 and FIG. 8, the retention volume of the peak top of each of the samples A, B, C, and D was on average 2.79 mL, 2.81 mL, 2.82 mL, and 2.76 mL, respectively and small compared to 3.04 mL for the pulp-derived CNF solution and 3.24 mL for pullulan. These results showed that the average molecular weight of the bacterial cellulose obtained by subjecting the strain NEDO-01 (*G. intermedius* strain SIID9587) to agitated culture was larger than that of the pulp-derived cellulose and more than $85.3 \times 10^4$ in terms of pullulan. Table 3 also showed that when the bacterial cellulose obtained by subjecting the strain NEDO-01 (*G. intermedius* strain SIID9587) to agitated culture was subjected to the gel permeation chromatography under the above conditions, the retention volume of the peak top of the chromatogram reached 2.5 mL (inclusive) to 3.0 mL (exclusive) since the retention volume of the peak top of each of the samples A, B, C, and D was in the range of 2.737 to 2.849 mL.

Example 7

Morphology of Bacterial Cellulose (1) Measurement of Fiber Width

The agitated-culture BC solution using the main-culture medium with glycerol of (1) of Example 2 and the mixer-treated stationary-culture BC solution of (2) of Example 2 were provided. These cellulose solutions were each adjusted to a concentration of about 0.001% (w/w), and then, 10 μL of each solution was added dropwise onto a Formvar-coated copper grid and air-dried. Subsequently, 5 μL of a 5% (w/v) gadolinium acetate aqueous solution was added dropwise thereto, and the excess solution was removed with a paper filter 10 seconds later for negative staining. The resultant was observed under a transmission electron microscope at an acceleration voltage of 80 kV and an observation magnification of 30,000 times to measure the width of cellulose fibers based on the observed image. The results are shown in FIG. 9.

Figure 9:
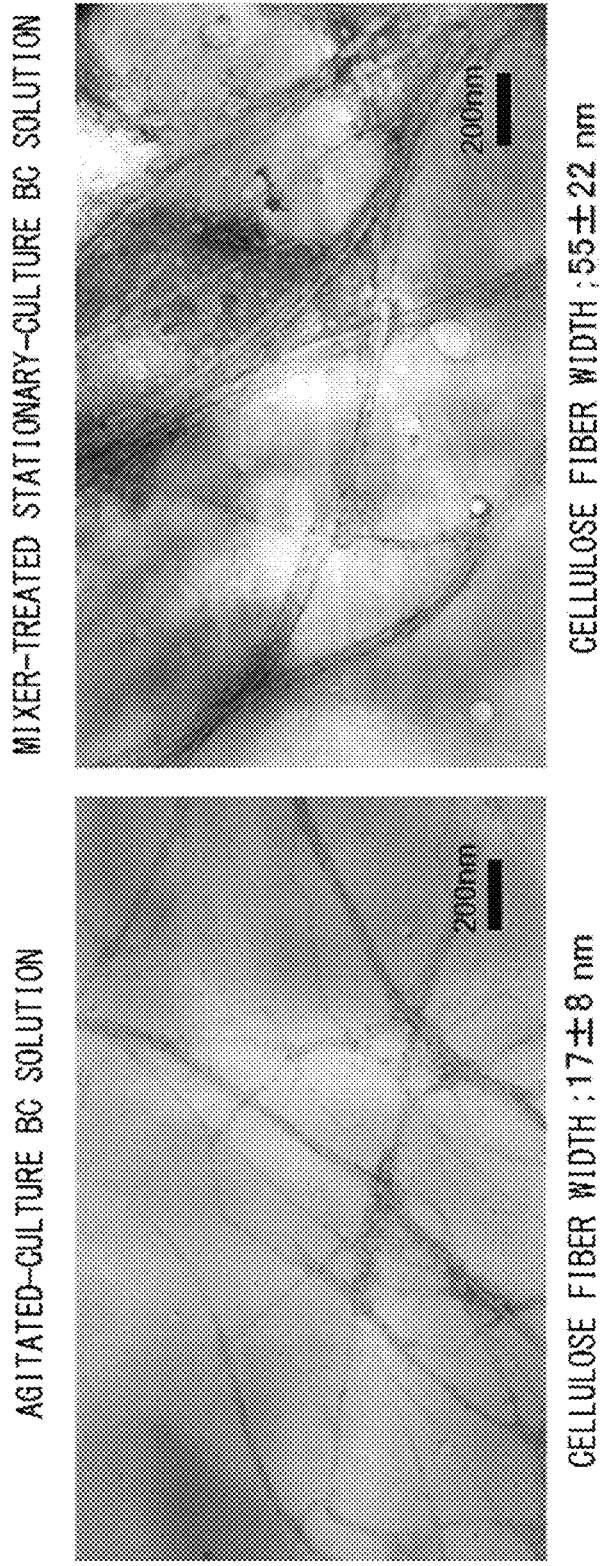
FIG. 9 is a pair of photographs showing the fiber widths and the transmission electron microscope-observed images of bacterial celluloses obtained by subjecting strain NEDO-01 (*G. intermedius* strain SIID9587) to aerated and agitated culture (agitated-culture BC solution) and stationary culture (mixer-treated stationary-culture BC solution).

As shown in FIG. 9, the width of the cellulose fibers was 17±8 nm for the agitated-culture BC solution, was prominently small compared to 55±22 nm for the mixer-treated stationary-culture BC solution, and had a small standard deviation. These results showed that the bacterial cellulose obtained by subjecting the strain NEDO-01 (*G. intermedius* strain SIID9587) to agitated culture formed fine and uniform fibers showing small variations in width between the fibers.

(2) Determination of Uniformity of Fiber Width and Aggregation State

Figure 10:
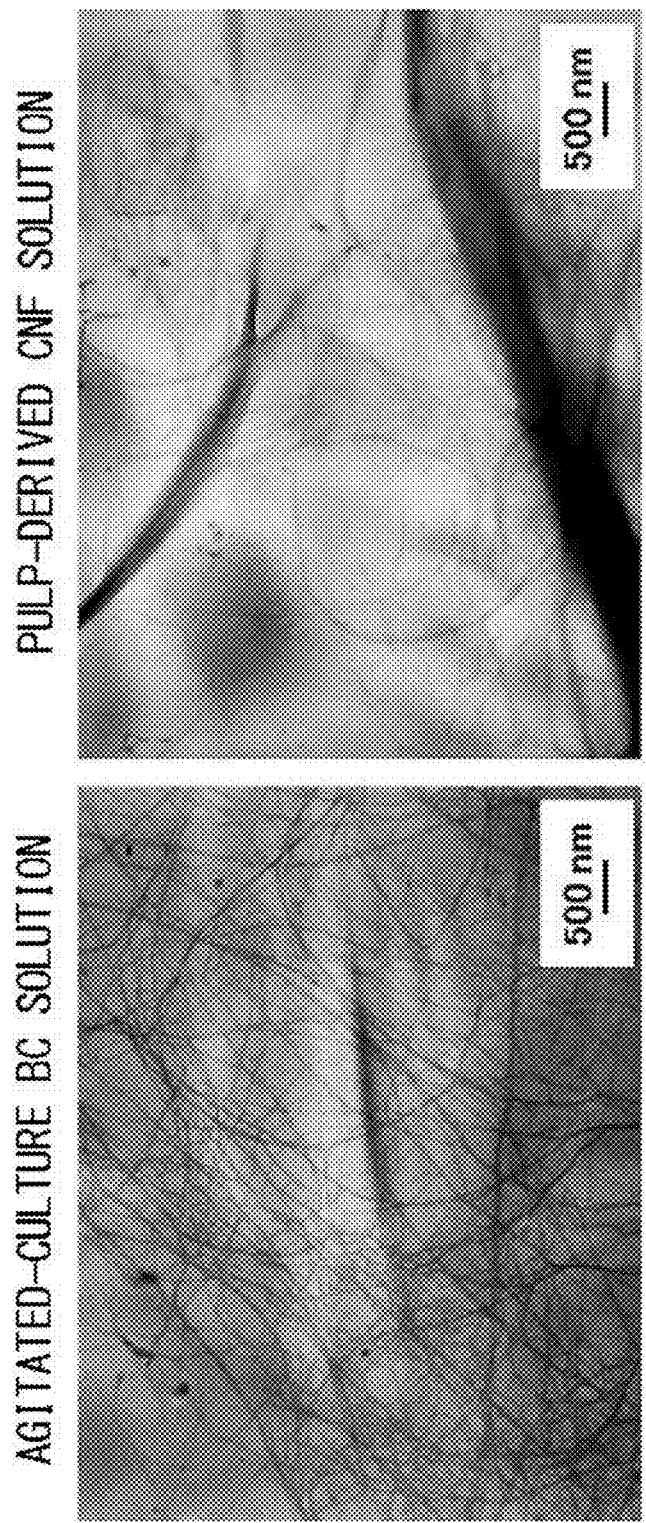
FIG. 10 is a pair of photographs showing the transmission electron microscope-observed images of a bacterial cellulose obtained by subjecting strain NEDO-01 (*G. intermedius* strain SIID9587) to aerated and agitated culture (agitated-culture BC solution) and a pulp-derived cellulose nanofiber (pulp-derived CNF solution).

The agitated-culture BC solution using the main-culture medium with BDF-B of (1) of Example 2 and the pulp-derived CNF solution of (1) of Example 3 were provided. These cellulose solutions were each adjusted to a concentration of about 0.01% (w/w), and then, the operation of spraying the solution on a Formvar-coated copper grid and drying it using a dryer was repeated 10 times. Subsequently, 5 μL of a 5% (w/v) gadolinium acetate aqueous solution was added dropwise thereto, and the excess solution was removed with a paper filter. In addition, the sequence of dropwise adding 5 μL of ultrapure water and then removing the excess solution with a paper filter was repeated 2 times, followed by negative staining by air-drying. The resultant was observed under a transmission electron microscope at an acceleration voltage of 80 kV and an observation magnification of 10,000 times. The results are shown in FIG. 10. It was also observed with crossed nicols using a polarizing microscope. The results are shown in FIG. 11.

As shown in FIG. 10, many cellulose fibers having comparable widths of the nano-scale were observed in the agitated-culture BC solution, whereas cellulose fibers having various widths, including widths as large as about 500 nm or more, were observed in the pulp-derived CNF solution. From these results, it was again determined that the bacterial cellulose obtained by subjecting the strain NEDO-01 (*G. intermedius* strain SIID9587) to agitated culture formed fibers having a uniform width of the nano-scale.

Figure 11:
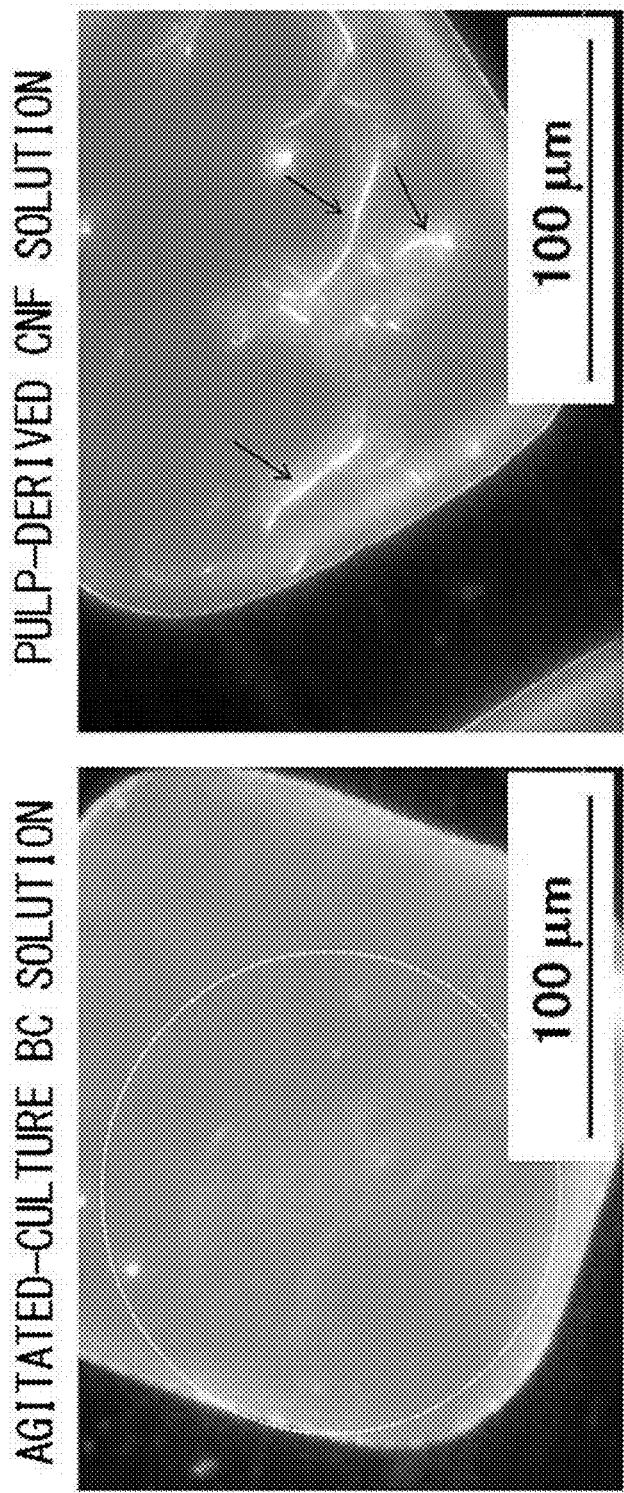
FIG. 11 is a pair of photographs showing the polarization microscope-observed images of a bacterial cellulose obtained by subjecting strain NEDO-01 (*G. intermedius* strain SIID9587) to aerated and agitated culture (agitated-culture BC solution) and a pulp-derived cellulose nanofiber (pulp-derived CNF solution).

As shown in FIG. 11, relatively thick fibers as shown by arrows were definitely observed in the pulp-derived CNF solution, whereas dim images were observed in the portion enclosed by a dotted line in the agitated-culture BC solution. These results showed that relatively thick fibers, such as submicrofibers and microfibers, were present for the pulp-derived cellulose, whereas thin fibers of the nano-scale were uniformly dispersed for the bacterial cellulose obtained by subjecting the strain NEDO-01 (*G. intermedius* strain SIID9587) to agitated culture.

Example 8

Evaluation of Bacterial Cellulose-Producing Ability (1) Production Ability in Stationary Culture Culture media were prepared in which pretreated BDF-B and reagent glycerol, respectively, were added in place of glucose as a carbon source in the LB culture medium, and called LB/BDF-B culture medium and LB/glycerol culture medium, respectively. The strain NEDO-01 (*G. intermedius* strain SIID9587), *Gluconacetobacter xylinus* strain ATCC53582, *Gluconacetobacter hansenii* strain ATCC23769, and *Gluconacetobacter xylinus* strain ATCC700178 (BPR2001) were each inoculated on each of the LB/glycerol culture medium and the LB/BDF-B culture medium and subjected to stationary culture at 30° C. for 7 days to form a gelled film. The operation of adding a 1% (w/v) NaOH aqueous solution thereto and performing autoclave treatment was repeated until the gelled film became white. Thereafter, the operation of adding water and performing autoclave treatment was repeated until pH reached 7 or less for purification. The bacterial cellulose obtained by drying after purification was measured for the absolute dry weight. The results are shown in FIG. 12.

Figure 12:
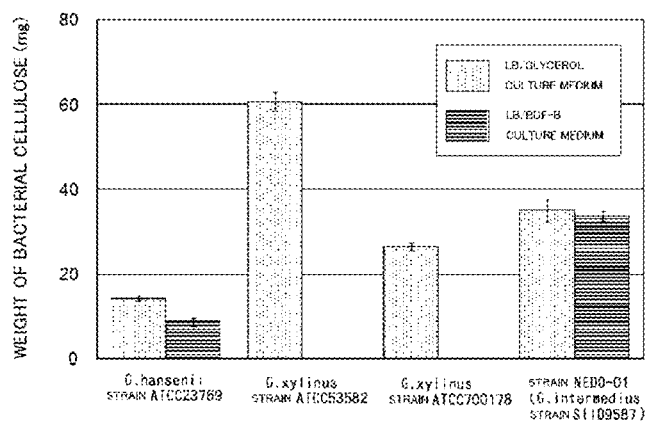
FIG. 12 is a graph showing the weight of bacterial celluloses obtained by subjecting strain NEDO-01 (*G. intermedius* strain SIID9587) and the known bacterial cellulose-producing bacteria *G. hansenii* strain ATCC23769, *G. xylinus* strain ATCC53582, and *G. xylinus* strain ATCC700178 (BPR2001) to stationary culture using reagent glycerol or BDF-B as a carbon source.

As shown in FIG. 12, G. hansenii strain ATCC23769 produced small weights of bacterial celluloses in both of the LB/glycerol culture medium and the LB/BDF-B culture medium. G. xylinus strain ATCC53582 and G. xylinus strain ATCC700178 (BPR2001) produced relatively large weights of bacterial celluloses in the LB/glycerol culture medium, whereas no bacterial cellulose production was observed in LB/BDF-B culture medium. In contrast, the strain NEDO-01 (G. intermedius strain SIID9587) produced comparably large weights of bacterial celluloses in both of the LB/glycerol culture medium and the LB/BDF-B culture medium. These results showed that the strain NEDO-01 (G. intermedius strain SIID9587) could efficiently produce a bacterial cellulose by being subjected to stationary culture using either reagent glycerol or BDF-B as a carbon source. Its feature of being capable of producing a bacterial cellulose using BDF-B as a carbon source is a feature which other compared strains do not have, also advantageous on the practical side in which the by-product can be utilized, and greatly contributes to a reduction in production cost.

(2) Production Ability in Agitated Culture

The strains NEDO-01 (G. intermedius strain SIID9587), strain ATCC53582, and strain ATCC23769 were each inoculated on 10 mL of the HS culture medium and subjected to stationary culture at 30° C. for 3 days for pre-preculture. Subsequently, the culture solution obtained by the pre-preculture was inoculated on 10 mL of the HS culture medium and subjected to stationary culture at 30° C. for 3 days for preculture. Then, 100 mL of each of the main-culture medium with glycerol and the main culture medium with BDF-B of (1) of Example 2 was placed in a bladed Erlenmeyer flask, and the preculture solution was inoculated in an amount corresponding to the same number of bacterial cells for each bacterial strain thereon and subjected to shake culture for 3 days under conditions of 150 rpm and 30° C. for the main culture. Subsequently, a bacterial cellulose in the main-culture solution was purified by the method described in (1) of Example 2. However, shake was performed at 60° C. and 80 rpm for 4 to 5 hours, followed by further shaking at 20° C. overnight. The purified bacterial cellulose was dried and measured for the absolute dry weight. The results are shown in FIG. 13.

Figure 13:
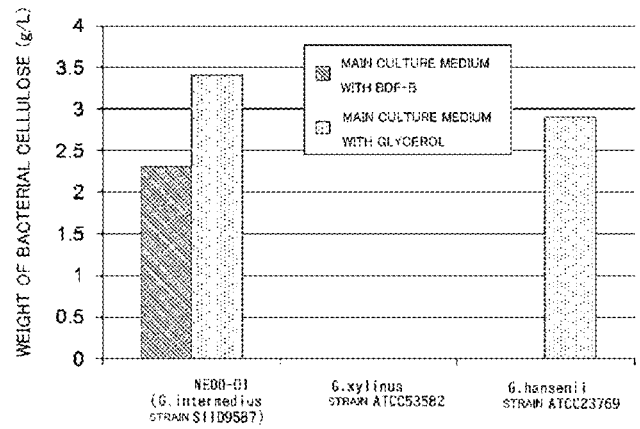
FIG. 13 is a graph showing the weight of bacterial celluloses obtained by subjecting strain NEDO-01 (*G. intermedius* strain SIID9587) and the known bacterial cellulose-producing bacteria, the strain ATCC53582 and the strain ATCC23769, to shake culture using reagent glycerol or BDF-B as a carbon source.

As shown in FIG. 13, G. xylinus strain ATCC53582 was not observed to produce a bacterial cellulose in each of the main-culture medium with glycerol and the main culture medium with BDF-B. For G. hansenii strain ATCC23769, the absolute dry weight of the bacterial cellulose was relatively large when the main-culture medium with glycerol was used, but no bacterial cellulose production was observed when the main culture medium with BDF-B was used. In contrast, for the strain NEDO-01 (G. intermedius strain SIID9587), the absolute dry weight of the bacterial cellulose was large when each of the main-culture medium with glycerol and the main culture medium with BDF-B was used. These results showed that the strain NEDO-01 (G. intermedius strain SIID9587) could efficiently produce the bacterial cellulose by either stationary culture or agitated culture using either reagent glycerol or BDF-B as a carbon source.

The invention claimed is:

1. A bacterial cellulose produced by a bacterium, having a physical characteristic of (a) and (b) below:
   (a) a transmittance of light at a wavelength of 500 nm of water containing the bacterial cellulose at a final concentration of 0.1±0.006% (w/w) of 35% or more; and
   (b) a retention volume of a peak top of a chromatogram in gel permeation chromatography performed under the following conditions i) to vi) of from 2.5 mL inclusive to 3.0 mL exclusive:
      i) column: a column 6.0 mm in inside diameter and 15 cm in length, packed with a methacrylate polymer having a particle diameter of 9 μm;
      ii) guard column: 4.6 mm in inside diameter and 15 cm in length;
      iii) column temperature: 35° C.;
      iv) feed flow rate: 0.07 mL/minute;
      v) eluent: a 40 to 42% (w/w) tetrabutylphosphonium hydroxide aqueous solution; and
      vi) final concentration of the bacterial cellulose in the eluent: 0.2% (w/w).

2. The bacterial cellulose according to claim 1, produced by the assimilation of a glycerol-containing by-product generated in producing a biodiesel fuel from vegetable oil using the bacterium.

3. The bacterial cellulose according to claim 1, produced by the assimilation of one or two or more selected from the group consisting of sugar, a sucrose-containing by-product generated in producing sugar, and hydrolysates thereof, and isomerized sugar, using the bacterium.

4. The bacterial cellulose according to claim 3, wherein the by-product is molasses.

5. The bacterial cellulose according to claim 1, wherein the bacterium is *Gluconacetobacter intermedius*.

6. The bacterial cellulose according to claim 1 produced by a bacterium, wherein the bacterium is *Gluconacetobacter intermedius* strain SIID9587 (accession number NITE BP-01495).

* * * * *